(12) United States Patent
Raines

(10) Patent No.: US 9,084,882 B1
(45) Date of Patent: Jul. 21, 2015

(54) LEADS FOR NEUROSTIMULATION AND METHODS OF ASSEMBLING SAME

(71) Applicant: Advanced Neuromodulation Systems, Inc., Plano, TX (US)

(72) Inventor: Aaron Raines, Dallas, TX (US)

(73) Assignee: ADVANCED NEUROMODULATION SYSTEMS, INC., Plano, TX (US)

( * ) Notice: Subject to any disclaimer, the term of this patent is extended or adjusted under 35 U.S.C. 154(b) by 0 days.

(21) Appl. No.: 14/191,065

(22) Filed: Feb. 26, 2014

(51) Int. Cl.
*A61N 1/00* (2006.01)
*A61N 1/05* (2006.01)

(52) U.S. Cl.
CPC .................................. *A61N 1/0553* (2013.01)

(58) Field of Classification Search
CPC ..... A61N 1/0553; A61N 1/05; A61N 1/0531; A61N 1/0534; A61N 1/08; A61N 1/16; A61N 1/0529; A61N 1/0551; A61N 1/372
See application file for complete search history.

(56) References Cited

U.S. PATENT DOCUMENTS

| | | | |
|---|---|---|---|
| 7,174,219 B2 | 2/2007 | Wahlstrand et al. | |
| 7,751,903 B2 | 7/2010 | Stevenson et al. | |
| 8,099,172 B2 | 1/2012 | Swanson | |
| 8,483,842 B2 | 7/2013 | Alexander et al. | |
| 2005/0070972 A1 | 3/2005 | Wahlstrand et al. | |
| 2009/0234402 A1* | 9/2009 | Marshall | 607/5 |
| 2012/0029342 A1 | 2/2012 | Kondabatni et al. | |
| 2012/0296190 A1 | 11/2012 | Kondabatni et al. | |

FOREIGN PATENT DOCUMENTS

| | | |
|---|---|---|
| EP | 1883449 B1 | 1/2009 |
| EP | 1742701 B1 | 8/2010 |
| EP | 2415499 A1 | 2/2012 |

* cited by examiner

Primary Examiner — Robert N Wieland

(57) ABSTRACT

The present disclosure provides systems and methods for neurostimulation. The system includes an electrode assembly for a paddle lead. The electrode assembly includes a wire wound around a bobbin to form an inductor. The wire is coupled to an input contact plate and an output contact plate. The bobbin is inserted into an aperture defined through an electrode, such that the inductor is substantially surrounded by the electrode.

20 Claims, 15 Drawing Sheets

LEADS FOR NEUROSTIMULATION AND METHODS OF ASSEMBLING SAME

A. FIELD OF THE DISCLOSURE

The present disclosure relates generally to neurostimulation methods and systems, and more particularly to paddle leads that are compatible with magnetic fields generated during a MRI scan.

B. BACKGROUND ART

Application of electrical fields to spinal nerve roots, spinal cord, and other nerve bundles for the purpose of chronic pain control has been actively practiced for some time. While a precise understanding of the interaction between applied electrical energy and the neural tissue is not understood, application of an electrical field to spinal nervous tissue (i.e., spinal nerve roots and spinal cord bundles) can effectively mask certain types of pain transmitted from regions of the body associated with the stimulated nerve tissue. Specifically, applying electrical energy to regions of the spinal cord associated with regions of the body afflicted with chronic pain can induce "paresthesia" (a subjective sensation of numbness or tingling) in the afflicted bodily regions. Thereby, paresthesia can effectively mask the transmission of non-acute pain sensations to the brain.

Each exterior region, or each dermatome, of the human body is associated with a particular spinal nerve root at a particular longitudinal spinal position. The head and neck regions are associated with C2-C8, the back regions extend from C2-S3, the central diaphragm is associated with spinal nerve roots between C3 and C5, the upper extremities correspond to C5 and T1, the thoracic wall extends from T1 to T11, the peripheral diaphragm is between T6 and T11, the abdominal wall is associated with T6-L1, lower extremities are located from L2 to S2, and the perineum from L4 to S4. In conventional neurostimulation, when a patient experiences pain in one of these regions, a neurostimulation lead is implanted adjacent to the spinal cord at the corresponding spinal position. For example, to address chronic pain sensations that commonly focus on the lower back and lower extremities using conventional techniques, a specific energy field is typically applied to a region between vertebrae levels T8 and T12. The specific energy field often stimulates a number of nerve fibers and structures of the spinal cord. By applying energy in this manner, the patient commonly experiences paresthesia over a relatively wide region of the patient's body from the lower back to the lower extremities.

Positioning of an applied electrical field relative to a physiological midline is also important. Nerve fibers extend between the brain and a nerve root along the same side of the dorsal column that the peripheral areas the fibers represent. Pain that is concentrated on only one side of the body is "unilateral" in nature. To address unilateral pain, electrical energy is applied to neural structures on the side of a dorsal column that directly corresponds to a side of the body subject to pain. Pain that is present on both sides of a patient is "bilateral". Accordingly, bilateral pain is addressed through application of electrical energy along both sides of the column and/or along a patient's physiological midline.

Percutaneous leads and paddle leads are the two most common types of lead designs that provide conductors to deliver stimulation pulses from an implantable pulse generator (IPG) to distal electrodes adjacent to the pertinent nerve tissue. Example commercially available leads include the QUATTRODE™, OCTRODE™, LAMITRODE™, TRI-POLE™, EXCLAIM™, and PENTA™ stimulation leads from St. Jude Medical, Inc. As shown in FIG. 1A, a conventional percutaneous lead 100 includes electrodes 101 that substantially conform to the body of the body portion of the lead. Due to the relatively small profile of percutaneous leads, percutaneous leads are typically positioned above the dura layer through the use of a Touhy-like needle. Specifically, the Touhy-like needle is passed through the skin, between desired vertebrae to open above the dura layer for the insertion of the percutaneous lead.

As shown in FIG. 1B, a conventional laminotomy or paddle lead 150 has a paddle configuration and typically possesses a plurality of electrodes 151 (commonly, eight, or sixteen) arranged in columns. Due to their dimensions and physical characteristics, conventional paddle leads may require a surgical procedure (a partial laminectomy) for implantation. Multi-column paddle leads enable more reliable positioning of a plurality of electrodes as compared to percutaneous leads. Also, paddle leads offer a more stable platform that tends to migrate less after implantation and that is capable of being sutured in place. Paddle leads also create a uni-directional electrical field and, hence, can be used in a more electrically efficient manner than at least some known percutaneous leads.

To supply suitable pain-managing electrical energy, multi-programmable IPGs enable a pattern of electrical pulses to be varied across the electrodes of a lead. Specifically, such systems enable electrodes of a connected stimulation lead to be set as an anode (+), as a cathode (−), or to a high-impedance state (OFF). As is well known, negatively charged ions and free electrons flow away from a cathode toward an anode. Consequently, using laminotomy lead 150 of FIG. 1B as an example, a range of very simple to very complex electrical fields can be created by defining different electrodes in various combinations of (+), (−), and OFF. Of course, in any instance, a functional combination must include at least one anode and at least one cathode (although in some cases, the "can" of the IPG can function as an anode).

One challenge faced by designers of neurostimulation and spinal cord stimulation systems is that the systems may be prone to heating and induced current when placed in the strong static, gradient, and/or radiofrequency (RF) magnetic fields of a magnetic resonance imaging (MRI) system. The heat and induced current are the results of the leads acting as antennas in the magnetic fields generated during a MRI scan. The heat and induced current may result in deterioration of stimulation thresholds and/or apply undesired heat to tissue in contact with the leads.

Yet many patients with an IPG and an implanted lead may require, or at the very least can benefit from, a MRI scan in the diagnosis or treatment of a medical condition. MRI scans have even been proposed as a visualization mechanism for lead implantation procedures. As such, it is desirable to have neurostimulation systems that are MRI-compatible. To this end, at least some known leads include inductor coils that are electrically coupled to the electrodes. The inductor coils are configured to prevent a flow of the induced current when the leads are exposed to different external magnetic fields.

The conventional leads include an elongated body that is formed from concentric inner and outer tubing. The wire conductors that join the electrodes and the inductor coils are located in an interior space between the inner and outer tubes. During manufacture, the wire conductors are inserted through the electrodes. However, the wire conductors are free-floating within the interior space and may also have relatively small diameters (e.g., less then microns). Accordingly, it may be difficult to capture and manipulate the wire conductors to join them to the electrode. The wire conductors are susceptible to breaking due to the small size. In addition, the electrical connections to the inductor coils (e.g., contacts and/or wires) and the wires of the inductor coils themselves may be small and, thus, difficult to manage and susceptible to breaking. Accordingly, the process of electrically joining the conductive components of the lead can be labor intensive and costly.

Therefore, a need remains for implantable leads and neurostimulation systems that are MRI-compatible and that are capable of being produced in a less costly manner than known leads and neurostimulation systems.

BRIEF SUMMARY OF THE DISCLOSURE

In one embodiment, the present disclosure is directed to an electrode assembly for use in a paddle lead. The electrode assembly includes a bobbin, an input contact plate coupled to a first end of the bobbin, an output contact plate coupled to a second end of the bobbin, a wire wound around the bobbin to form an inductor, wherein a first termination of the wire is electrically coupled to the input contact plate, and wherein a second termination of the wire is electrically coupled to the output contact plate, and an electrode comprising an application surface and having an aperture defined therethrough, wherein the bobbin is inserted into the aperture such that the inductor is substantially surrounded by the electrode.

In another embodiment, the present disclosure is directed to a paddle lead for applying neurostimulation to a patient. The paddle lead includes a carrier board, a plurality of electrode assemblies coupled to the carrier board, and an over mold substantially encapsulating the carrier board and the plurality of electrode assemblies. Each of the plurality of electrode assemblies includes a bobbin, an input contact plate coupled to a first end of the bobbin, an output contact plate coupled to a second end of the bobbin, a wire wound around the bobbin to form an inductor, wherein a first termination of the wire is electrically coupled to the input contact plate, and wherein a second termination of the wire is electrically coupled to the output contact plate, and an electrode comprising an application surface and having an aperture defined therethrough, wherein the bobbin is inserted in the aperture such that the inductor is substantially surrounded by the electrode.

In another embodiment, the present disclosure is directed to a method for assembling a paddle lead for applying neurostimulation to a patient. The method includes winding a wire around a bobbin to form an inductor, welding a first termination of the wire to an input contact plate that is coupled to a first end of the bobbin, welding a second termination of the wire to an output contact plate that is coupled to a second end of the bobbin, inserting the bobbin into an aperture defined through an electrode to form an electrode assembly, the bobbin inserted such that the inductor is substantially surrounded by the electrode, and coupling the electrode assembly to a carrier board.

The foregoing and other aspects, features, details, utilities and advantages of the present disclosure will be apparent from reading the following description and claims, and from reviewing the accompanying drawings.

BRIEF DESCRIPTION OF THE DRAWINGS

Corresponding reference characters indicate corresponding parts throughout the several views of the drawings.

DETAILED DESCRIPTION OF THE DISCLOSURE

Figure 1A:
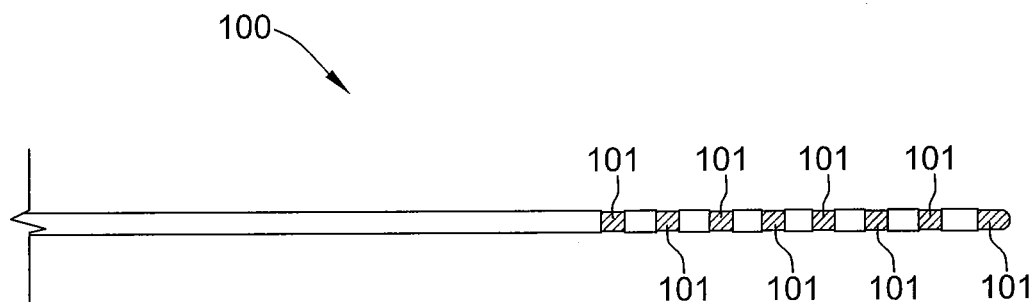
FIG. 1A is a schematic diagram of a conventional percutaneous lead.
Figure 1B:
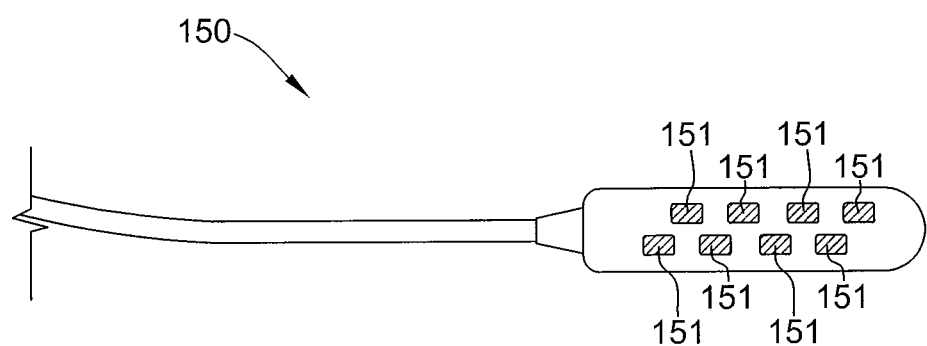
FIG. 1B is a schematic diagram of a conventional paddle lead.

The present disclosure provides systems and methods for neurostimulation. The system includes an electrode assembly for a paddle lead. The electrode assembly includes a wire wound around a bobbin to form an inductor. The wire is coupled to an input contact plate and an output contact plate. The bobbin is inserted into an aperture defined through an electrode, such that the inductor is substantially surrounded by the electrode.

I. Definitions

Unless defined otherwise, technical and scientific terms used herein have the same meaning as commonly understood by one of ordinary skill in the art to which this disclosure belongs. For purposes of the present disclosure, the following terms are defined below.

As used herein, the use of the word "a" or "an" when used in conjunction with the term "comprising" in the claims and/or the specification may mean "one", but it is also consistent with the meaning of "one or more", "at least one", and "one or more than one". Still further, the terms "having", "including", "containing" and "comprising" are interchangeable and one of skill in the art is cognizant that these terms are open-ended terms. Some embodiments may consist of or consist essentially of one or more elements, method steps, and/or methods of the disclosure. It is contemplated that any method or composition described herein can be implemented with respect to any other method or composition described herein.

As used herein, the use of the term "dorsal column" refers to conducting pathways in the spinal cord that are located in the dorsal portion of the spinal cord between the posterior horns, and which includes afferent somatosensory neurons. The dorsal column is also known as the posterior funiculus.

As used herein, "spinal cord," "spinal nervous tissue associated with a vertebral segment," "nervous tissue associated with a vertebral segment" or "spinal cord associated with a vertebral segment or level" includes any spinal nervous tissue associated with a vertebral level or segment. Those of skill in the art are aware that the spinal cord and tissue associated therewith are associated with cervical, thoracic and lumbar vertebrae. As used herein, C1 refers to cervical vertebral segment 1, C2 refers to cervical vertebral segment 2, and so on. T1 refers to thoracic vertebral segment 1, T2 refers to thoracic vertebral segment 2, and so on. L1 refers to lumbar vertebral segment 1, L2 refers to lumbar vertebral segment 2, and so on, unless otherwise specifically noted. In certain cases, spinal cord nerve roots leave the bony spine at a vertebral level different from the vertebral segment with which the root is associated. For example, the T1 nerve root leaves the spinal cord myelum at an area located behind vertebral body T8-T9 but leaves the bony spine between T11 and T12.

As used herein the term "chronic pain" refers to a persistent state of pain experienced for a substantial amount of time (e.g., longer than three months).

As used herein the term "complex regional pain syndrome" or "CRPS" refers to painful conditions that usually affect the distal part of an upper or lower extremity and are associated with characteristic clinical phenomena. CRPS is divided into two subtypes CRPS Type I and CRPS Type II. Generally, the clinical characteristics of Type I are the same as seen in Type II. The central difference between Type I and Type II is that Type II typically occurs following a sensory nerve injury whereas Type I occurs in the absence of any known nerve injury.

II. Organization of the Nervous System

The nervous system includes two general components, the central nervous system, which is composed of the brain and the spinal cord, and the peripheral nervous system, which is composed of ganglia or dorsal root ganglia and the peripheral nerves that lie outside the brain and the spinal cord. Those of skill in the art will appreciate that the components of the nervous system may be linguistically separated and categorized, but functionally they are interconnected and interactive.

Figure 2:
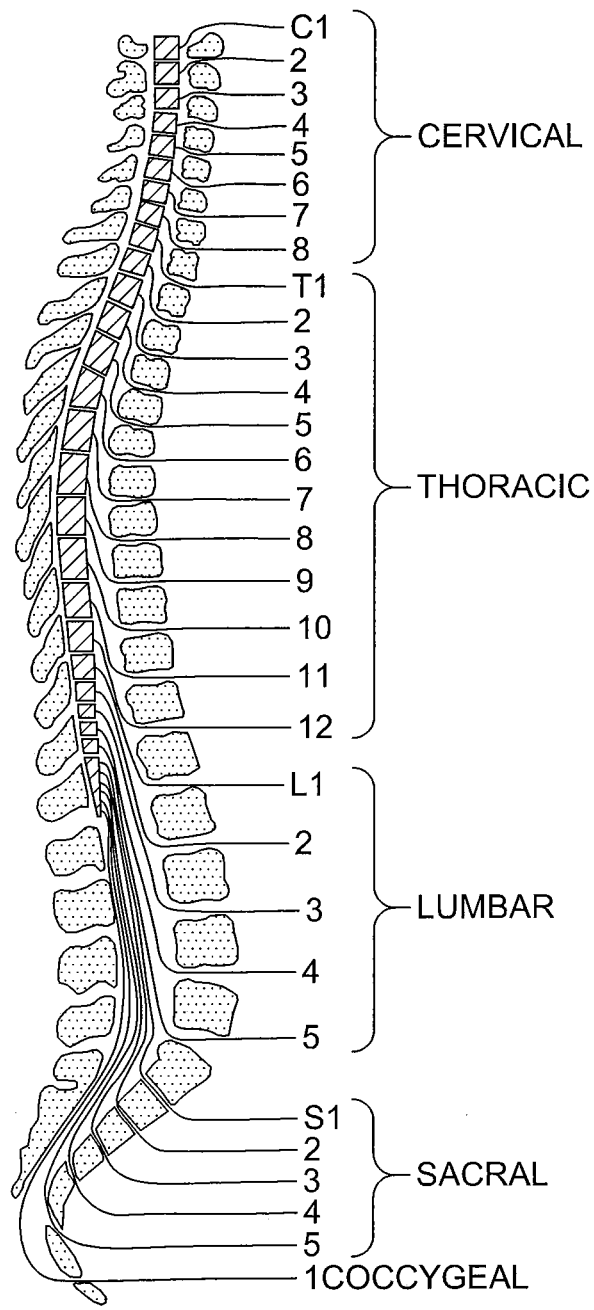
FIG. 2 is a schematic diagram of the spinal cord and the nerve roots in relation to the vertebral spinal canal.

The central nervous system includes the brain and spinal cord, which together function as the principal integrator of sensory input and motor output. In general terms, the brain consists of the cerebrum (cerebral hemispheres and the diencephalons), the brainstem (midbrain, pons, and medulla), and the cerebellum. The spinal cord is organized into segments, for example, there are 8 cervical (C1-C8), 12 thoracic (T1-T12), 5 lumbar (L1-L5), 5 sacral (S1-S5), and 1 cocygeal (Co1) spinal segments. In adults, the spinal cord typically ends at the level of the L1 or L2 vertebral bones. As shown in FIG. 2, the nerve roots travel downward to reach their exit points at the appropriate levels. Left and right sensory and motor nerve roots arise from each segment of the spinal cord except for the C1 and Co1 segments, which have no sensory roots. Associated sensory and motor nerve roots fuse to form a single mixed spinal nerve for each segment. The mixed spinal nerves further fuse and intermingle peripherally to form plexuses and nerve branches.

The peripheral nervous system is divided into the autonomic system (parasympathetic and sympathetic), the somatic system, and the enteric system. The term peripheral nerve is intended to include both motor and sensory neurons and neuronal bundles of the autonomic system, the somatic system, and the enteric system that reside outside of the spinal cord and the brain. Peripheral nerve ganglia and nerves located outside of the brain and spinal cord are also described by the term peripheral nerve.

III. Stimulation Leads and Systems

Figure 3:
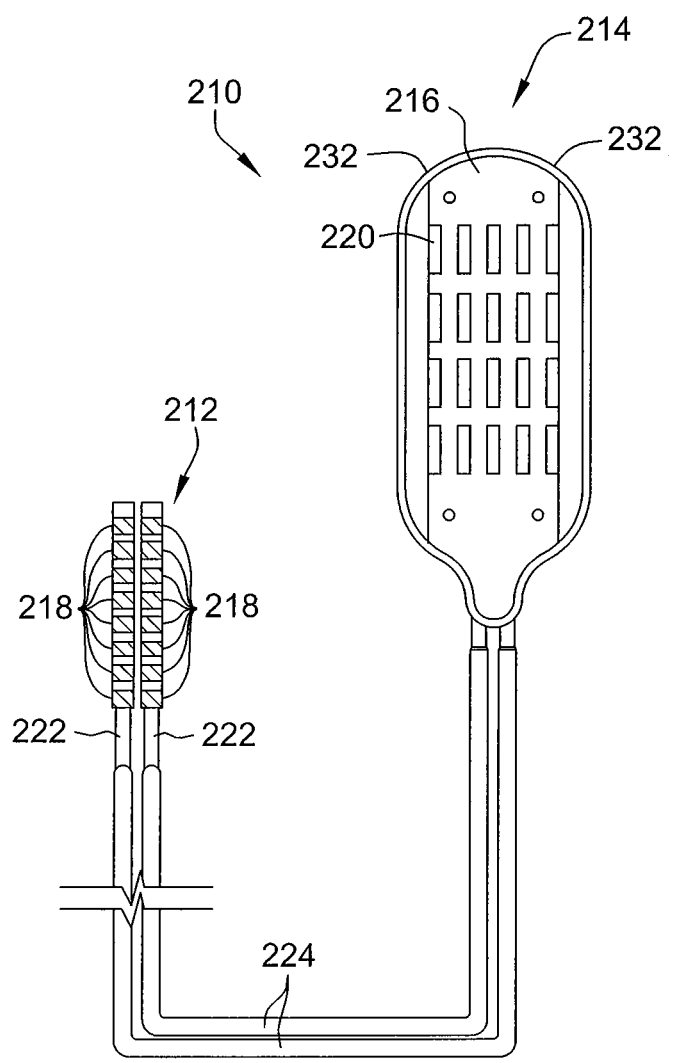
FIG. 3 is a schematic diagram of a paddle lead according to one embodiment.

FIG. 3 is a schematic diagram of a paddle lead 210 according to one embodiment. Paddle lead 210 includes a proximal end 212 and a distal end 214. Proximal end 212 includes a plurality of electrically conductive terminals 218. Distal end 214 includes a plurality of electrically conductive electrodes 220 arranged within a substantially flat, thin paddle 216. Electrodes 220 are mutually separated by insulative material of paddle 216. For a paddle structure adapted for implantation within a cervical vertebral level, electrodes 220 are may be spaced apart 1.5 mm laterally and 2.5 mm longitudinally. For a paddle adapted for implantation within a thoracic vertebral level, electrodes 220 may be spaced apart by 1.0 mm laterally and 2 mm or 3 mm longitudinally. Conductors 222 (which are embedded within the insulative material of the lead body) electrically connect electrodes 220 to terminals 218.

In the embodiment shown in FIG. 3, paddle 216 includes five columns and four rows of electrodes 220 arranged in a grid configuration, for a total of twenty electrodes 220. Alternative numbers of columns and rows may be employed. For example, in some embodiments, thirty-two or more electrodes are distributed into multiple rows and multiple columns. Also, every row need not contain the same number of columns. For example, a number of rows can include a "tripole" design having three columns of electrodes while additional rows can include five or more columns of electrodes to enable a greater amount of electrical field resolution. The multiple columns of electrodes 220 enable lateral control of the applied electrical field to stimulate the exact lateral position of the pertinent nerve fiber(s), as described herein.

Specifically, it may be desirable to selectively stimulate a given dorsal column fiber that is associated with an afflicted region of the patient's body without affecting other regions of the patient's body. The multiple columns of paddles according to representative embodiments provide sufficient resolution to relatively finely control the stimulation of one or several specific fibers, as described herein. Additionally, the multiple columns provide a degree of positional tolerance during the surgical placement of paddle 216 within the epidural space, as any one of the columns may be used to stimulate the pertinent nerve fiber(s). Also, if paddle 216 is displaced relative to the pertinent nerve fibers subsequent to implantation (e.g., due to lead migration), the stimulation pattern applied by a pulse generator can be shifted between columns to compensate for the displacement.

The multiple rows of electrodes 220 enable multiple pain locations to be treated with a single implanted lead. Specifically, a first row can be used to treat a first pain complaint (e.g., pain in the lower extremities) and a second row can be used to treat a second pain location (e.g., post-laminectomy pain in the back). Furthermore, by separating the first and second rows by one or more "buffer" rows of high-impedance electrodes 220, the stimulation in the first and second rows may occur on a substantially independent basis. Specifically, anodes in the second row will have relatively minimal effect on the field distribution generated by cathodes in the first row.

In some embodiments, paddle lead 210 can be implanted within a patient such that electrodes 220 are positioned within the cervical or thoracic spinal levels. After implantation, an electrode combination on a first row of electrodes 220 can be determined that is effective for a first pain location with minimal effects on other regions of the body. The first pain location can be addressed by stimulating a specific dorsal column fiber due to the relatively fine electrical field resolution achievable by the multiple columns. Then, another electrode combination on a second row of electrodes 220 can be determined for a second pain location with minimal effects on other regions of the body. The second pain location could be addressed by stimulating another dorsal column fiber as an example. After the determination of the appropriate electrodes 220 for stimulation, a patient's implantable pulse generator (IPG) can be programmed to deliver pulses using the first and second rows according to the determined electrode combinations.

When determining the appropriate electrode configurations, the selection of electrodes 220 to function as anodes can often facilitate isolation of the applied electrical field to desired fibers and other neural structures. Specifically, the selection of an electrode 220 to function as an anode at a position adjacent to another electrode 220 functioning as a cathode causes the resulting electron/ion flow to be limited to tissues immediately surrounding the two electrodes 220. By alternating through a plurality of anode/cathode combinations, as described herein, it is possible to improve resolution in the stimulation of dorsal column fibers. Also, it is possible to confine the applied electrical field to or away from a periphery of paddle 216.

The operation of anodes can also be used to hyperpolarize neural tissue. Depending on the anode amplitude and the proximity to the pertinent neural tissue, the hyperpolarization can be used to prevent selected neural tissue from propagating action potentials. The hyperpolarization can also be used to prevent an adjacent cathode from initiating propagation of an action potential beginning at the selected neural tissue.

Multiple columns of electrodes 220 also enable lateral "steering" of the electrical field using a single channel pulse generator. A single channel pulse generator refers to a pulse generator that provides an equal magnitude pulse to each active electrode 220 at a given time. Specifically, each electrode 220 is either "active" (i.e., it is coupled to the pulse generator output during pulse generation by a suitable gate or switch) or "inactive" (i.e., the gate or switch does not couple the electrode to the pulse generator output). Each "active" electrode 220 experiences the same amplitude; only the polarity varies depending upon whether electrode 220 is set as a cathode or anode as defined by positions of respective gates and/or switches. The steering of the electrical field occurs by selecting appropriate states for each of electrodes 220.

Conductors 222 are carried in sheaths 224. In some embodiments, each sheath 224 carries eight conductors 222. With only two sheaths 224 with eight conductors each, there would only be sixteen conductors 222. To accommodate the lower number of conductors 222 than electrodes 220, multiple electrodes 220 may be coupled to the same conductor 222 (and, hence, to a common terminal 218).

In some embodiments, other electrode designs can be employed to minimize the number of conductors 222 required to support the various electrodes 220. For example, a relatively large number of electrodes 220 (e.g., thirty-two, sixty-four, and greater) could be utilized on paddle 216. Electrodes 220 could be coupled to one or several electrical gates (e.g., as deposited on a flex circuit). The electrical gates can be controllably configured to couple each electrode 220 to a conductor 222 carrying cathode pulses, to couple each electrode 220 to an anode termination, or to maintain each electrode 220 at a high impedance state. The electrical gates could be controlled using a main controller, such as a logic circuit, on the paddle 216 that is coupled to a data line conductor 222. The data line conductor 222 communicates signals from an IPG that identify the desired electrode states, and the main controller responds to the signals by setting the states of the electrical gates as appropriate.

In another embodiment, a cathode conductor line 222 and an anode conductor line 222 are provided in one or several lead bodies along with a plurality of optical fibers. The optical fibers are used to carry optical control signals that control the electrode states. Specifically, paddle 216 includes photodetectors (e.g., photodiodes) that gate connections to anode conductor line 222 and cathode conductor line 222. The use of optical fibers to carry optical control signals may be advantageous, because the diameter of optical fibers suitable for such functionality is smaller than electrical conductors 222. Therefore, a larger number of electrodes 220 (as compared to using a separate electrical conductor 222 for each electrode 220) can be independently controlled while maintaining the lead body diameters at an acceptable size.

Terminals 218 are preferably formed of a non-corrosive, highly conductive material. Examples of such material include stainless steel, MP35N, platinum, and platinum alloys. In one embodiment, terminals 218 and are formed of a platinum-iridium alloy. Each conductor 222 is formed of a conductive material that exhibits desired mechanical properties of low resistance, corrosion resistance, flexibility, and strength. While conventional stranded bundles of stainless steel, MP35N, platinum, platinum-iridium alloy, drawn-brazed silver (DBS) or the like can be used, one embodiment uses conductors 222 formed of multi-strands of drawn-filled tubes (DFT). Each strand is formed of a low resistance material and is encased in a high strength material (preferably, metal). A selected number of "sub-strands" are wound and coated with an insulative material. With regard to the operating environment of representative embodiments, such insulative material protects an individual conductor 222 if its respective sheath 224 is breached during use.

In addition to providing the requisite strength, flexibility, and resistance to fatigue, conductors 222 formed of multi-strands of drawn-filled tubes, in accordance with the above description, provide a low resistance alternative to other materials. Specifically, a stranded wire, or even a coiled wire, of approximately 60 cm and formed of MP35N or stainless steel or the like may have a measured resistance in excess of 30 ohms. In contrast, for the same length, a wire formed of multi-strands of drawn-filled tubes could have a resistance less than 4 ohms.

Sheaths 224 and paddle 216 are preferably formed from a medical grade, substantially inert material, for example, polyurethane, silicone, or the like. Importantly, such material should be non-reactive to the environment of the human body, provide a flexible and durable (i.e., fatigue resistant) exterior structure for the components of paddle lead 210, and insulate adjacent terminals 218 and/or electrodes 220.

Paddle 216 may be fabricated to possess a substantially flat profile. Alternatively, paddle 216 may have an arcuate or bowed profile. In the embodiment shown in FIG. 3, wing structures 232 are formed on each longitudinal side of paddle 216. Wing structures 232 may be formed for the purpose of retaining paddle 216 within the central portion of the epidural space. In some embodiments, one or more electrodes 220 may be disposed on wing structures 232.

Figure 4:
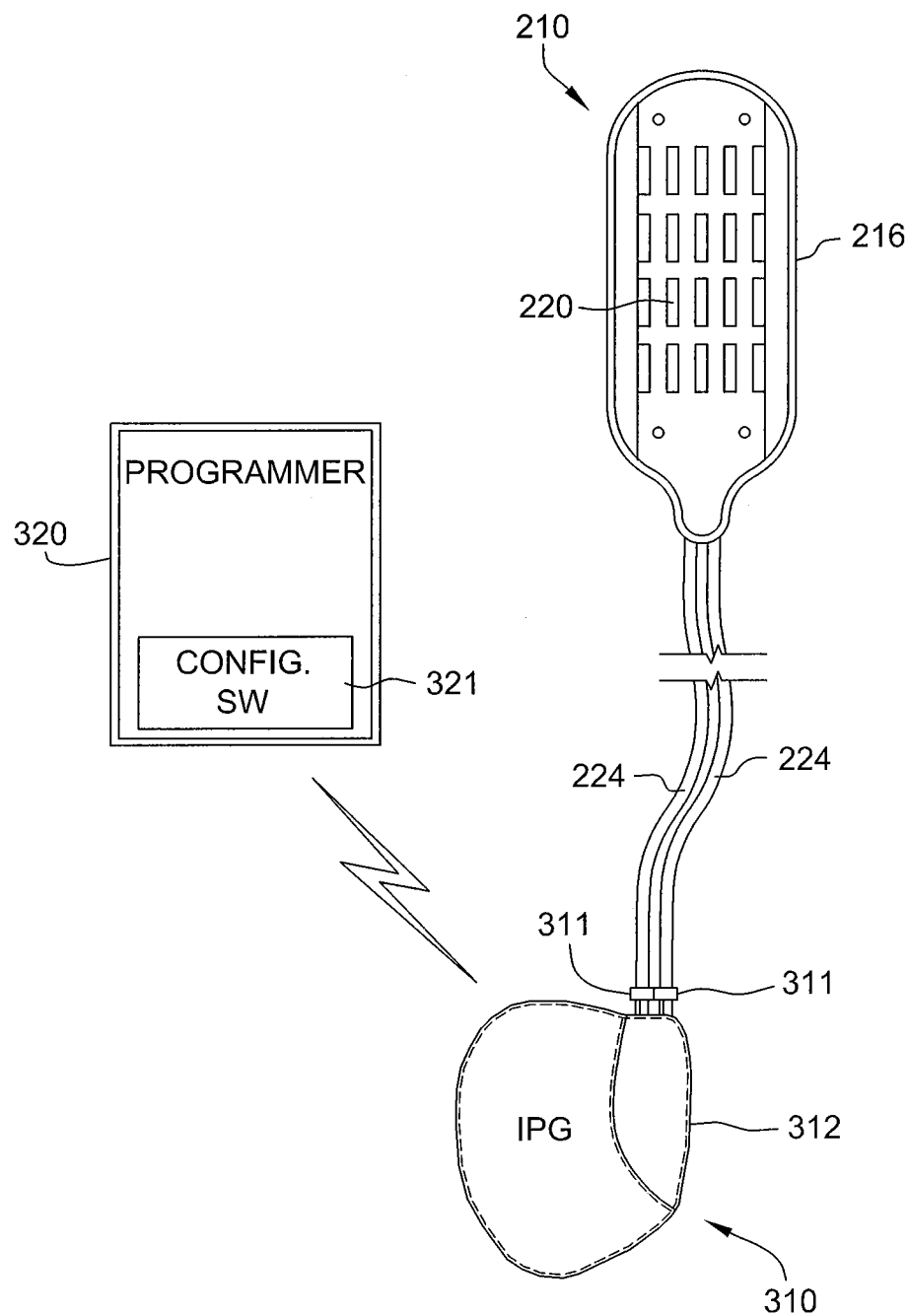
FIG. 4 is a schematic diagram of a paddle lead coupled to an implantable pulse generator in communication with a wireless programmer device according to one embodiment.

FIG. 4 depicts paddle lead 210 coupled to an IPG 310 which is in wireless communication with a programmer device 320. An example of a commercially available IPG is the Eon™ Rechargeable IPG from St. Jude Medical, Inc.

(Plano, Tex.), although any suitable IPG, such as RF powered devices, could be alternatively employed.

As shown in FIG. 4, paddle lead 210 is coupled to header ports 311 of IPG 310. Each header port 311 electrically couples respective terminals 218 (shown in FIG. 3) to a switch matrix (not shown) within IPG 310.

The switch matrix selectively connects the pulse generating circuitry (not shown) of IPG 310 to terminals 218, and, hence to electrodes 220. A sealed portion 312 of IPG 310 contains pulse generating circuitry, communication circuitry, control circuitry, and a battery (not shown) within an enclosure to protect the components after implantation within a patient. The control circuitry may comprise a microprocessor, one or more ASICs, and/or any suitable circuitry for controlling the pulse generating circuitry. The control circuitry controls the pulse generating circuitry to apply electrical pulses to the patient via electrodes 220 of paddle 216 according to multiple pulse parameters (e.g., pulse amplitude, pulse width, pulse frequency, etc.). Electrodes 220 are set to function as cathodes or anodes or set to a high-impedance state for a given pulse according to the couplings provided by the switch matrix. The electrode states may be changed between pulses.

When paddle lead 210 is initially implanted within the patient, a determination of the set(s) of pulse parameters and the electrode configuration(s) that may effectively treat the patient's condition is made. The determination or programming typically occurs through a physician's interaction with configuration software 321 executed on programmer device 320. Configuration software 321 steps the physician through a number of parameters and electrode configurations based on a trolling algorithm. In some embodiments, the electrode configurations are stepped through by laterally "steering" the electrical field by moving the anodes and/or cathodes along a row of the paddle. The patient provides feedback to the physician regarding the perceived stimulation that occurs in response the pulse parameters and electrode configuration(s). The physician may effect changes to the parameters and electrode configuration(s) until optimal pulse parameters and electrode configuration(s) are determined. The final pulse parameters and configurations are stored within IPG 310 for subsequent use. The pulse parameters and configurations are used by IPG 310 to control the electrical stimulation provided to the patient via paddle lead 210. Although single channel IPGs have been described according to some embodiments, multiple current or voltage source IPGs could alternatively be employed.

FIGS. 5-15 illustrate one embodiment of a method for assembling a paddle lead, such as paddle lead 210 (shown in FIGS. 3 and 4).

Figure 5:
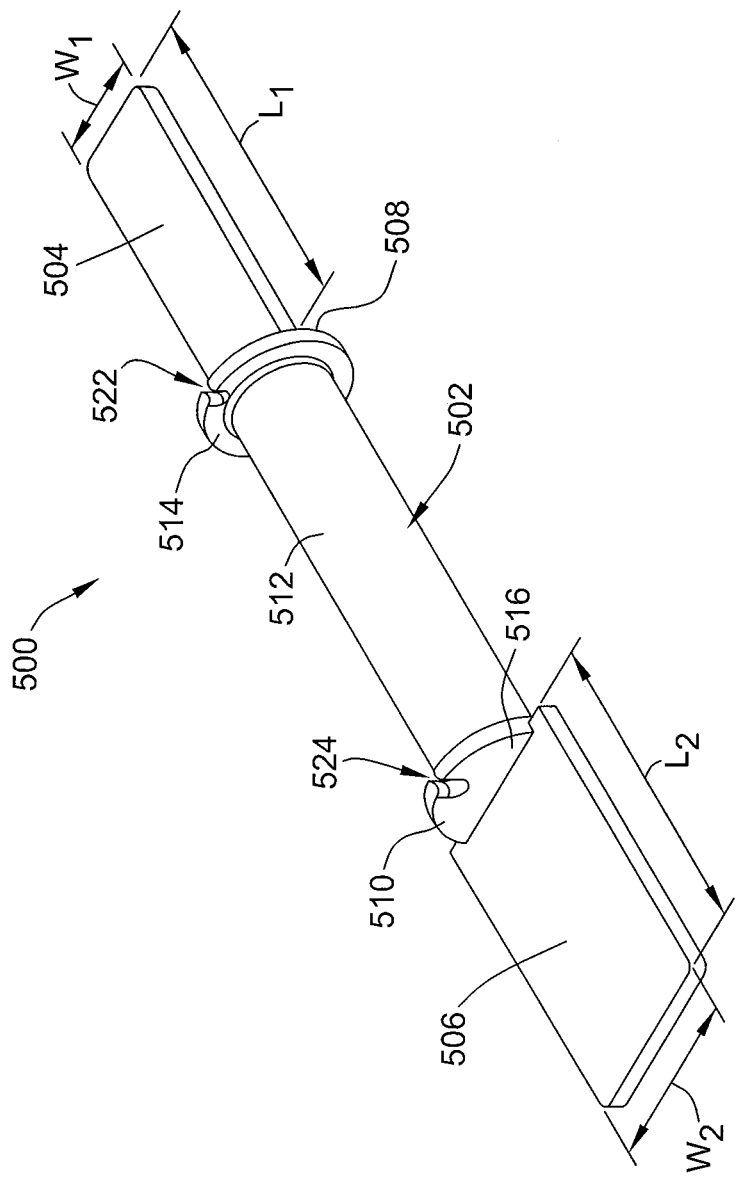
FIG. 5 is a perspective view of an initial assembly for assembling a paddle lead according to one embodiment.

FIG. 5 is a perspective view of an initial assembly 500 for assembling a paddle lead. Assembly 100 includes a bobbin 502, an input contact plate 504, and an output contact plate 506. In this embodiment, input and output contact plates 504 and 506 are metallic, and bobbin 502 is polymer.

Input contact plate 504 engages a first end 508 of bobbin 502, and output contact plate 506 engages an opposite second end 510 of bobbin 502. Input and output contact plates 504 and 506 may be formed, for example, using a progressive die, and bobbin 502 may be formed using an injection molding process. That is, input and output contact plates 504 and 506 are inserted in a mold, and a polymer is injected into the mold and cured to form bobbin 502 extending between input and output contact plates 504 and 506.

As shown in FIG. 5, input and output contact plates 504 and 506 are substantially planar. Input contact plate 504 has a length, $L_1$, and a width, $W_1$, and output contact plate 506 has a length $L_2$, and a width, $W_2$. In this embodiment, $L_1$ and $L_2$ are substantially equal, and $W_2$ is greater than $W_1$, such that output contact plate 506 is wider than input contact plate 504.

Bobbin 502 includes a substantially cylindrical body 512, a first disc 514 at first end 508 and a second disc 516 at second end 510. First and second discs 514 and 516 have a larger diameter than body 512. A first notch 522 is defined in first disc 514, and a second notch 524 is defined in second disc 516.

Figure 6:
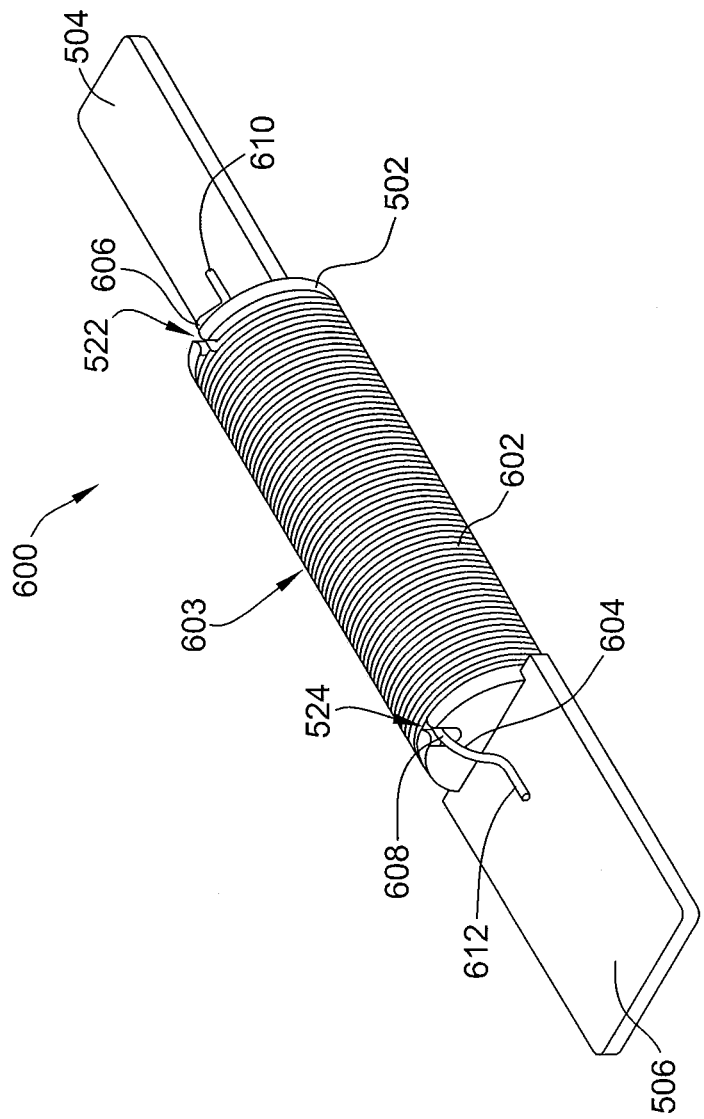
FIG. 6 is a perspective view of an intermediate assembly according to one embodiment.

FIG. 6 is a perspective view of an intermediate assembly 600. In intermediate assembly 600, a wire 602 is wound around bobbin 502, forming an inductor 603. In this embodiment, wire 602 is a 1 mil wire. Alternatively, wire 602 may have any dimensions that enable intermediate assembly 600 to function as described herein.

Inductor 603 functions as an RF choke tuned to a particular frequency (e.g., 64 MHz). Wire 602 is covered in insulation 604. As shown in FIG. 6, a first end 606 of wire 602 is threaded through first notch 522, and a second end 608 of wire 602 is threaded through second notch 524. Wire 602 is electrically coupled to input and output contact plates 504 and 506. Specifically, a first termination 610 of wire 602 is welded to input contact plates 504, and a second termination 612 of wire 602 is welded to output contact plate 506.

Figure 7:
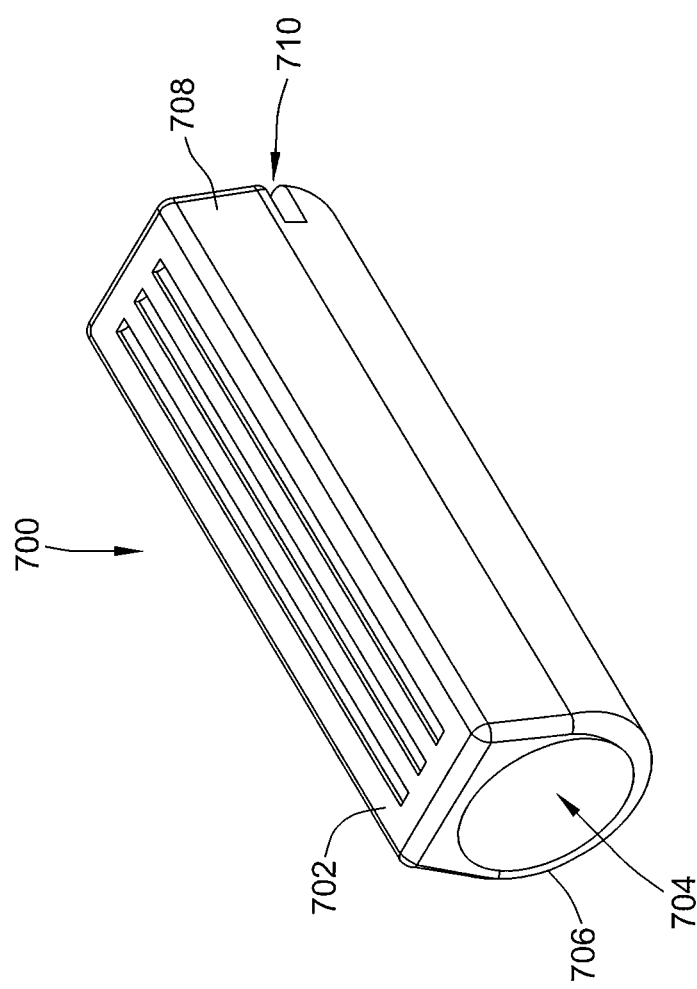
FIG. 7 is a perspective view of an electrode according to one embodiment.

FIG. 7 is a perspective view of an electrode 700. Electrode 700 is formed of a conductive material, such as, for example, stainless steel, MP35N, platinum, and platinum alloys. In one embodiment, electrode 700 is formed of a platinum-iridium alloy. Electrode 700 includes a substantially planar application surface 702 that contacts the patient during electrical stimulation. A substantially circular aperture 704 is defined through electrode 700 and extends from a first end 706 to a second end 708. Further, a pair of notches 710 is defined in electrode 700 at second end 708.

Figure 8:
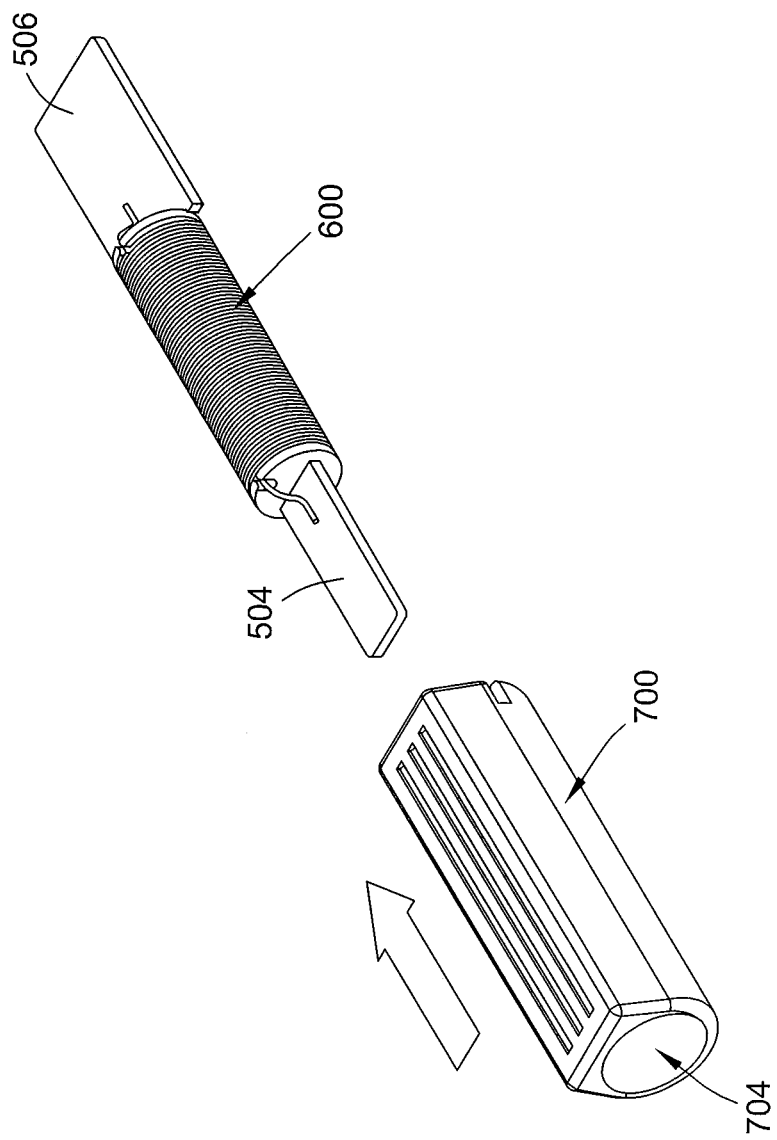
FIG. 8 is a perspective view of the intermediate assembly shown in FIG. 6 and the electrode shown in FIG. 7.
Figure 9:
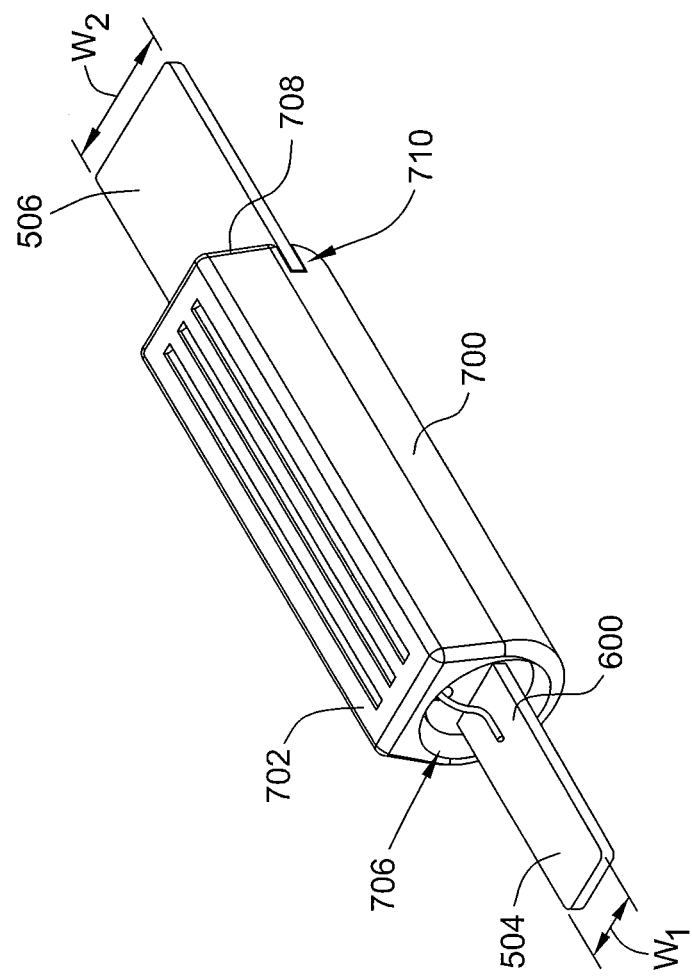
FIG. 9 is a perspective view of the intermediate assembly shown in FIG. 6 and the electrode shown in FIG. 7.

FIGS. 8 and 9 are perspective views of intermediate assembly 600 and electrode 700. As shown in FIGS. 8 and 9, electrode 700 slides over intermediate assembly 600 such that electrode 700 engages intermediate assembly 600. Specifically, intermediate assembly 600 is inserted into electrode 700 with input contact plate 504 entering aperture 704 first. Intermediate assembly 600 is threaded through aperture 704 until output contact plate 506 engages notches 710. That is, width $W_1$ of input contact plate 504 is smaller than a diameter of aperture 704, but width $W_2$ of output contact plate 506 is larger than the diameter of aperture 704.

By engaging notches 710, output contact plate 506, and by extension, wire 602, is electrically coupled to electrode 700. After intermediate assembly 600 is inserted into electrode 700, intermediate assembly 600 is further secured to electrode 700 using a suitable epoxy (not shown). Specifically, epoxy is applied and cured inside aperture 704 proximate first end 706 and second end 708. The epoxy and insulation 604 prevent wire 602 from electrically contacting electrode 700 directly. Further, epoxy prevents fluids from coming in contact with inductor 603, facilitating stability and reliability of inductor 603.

Figure 10:
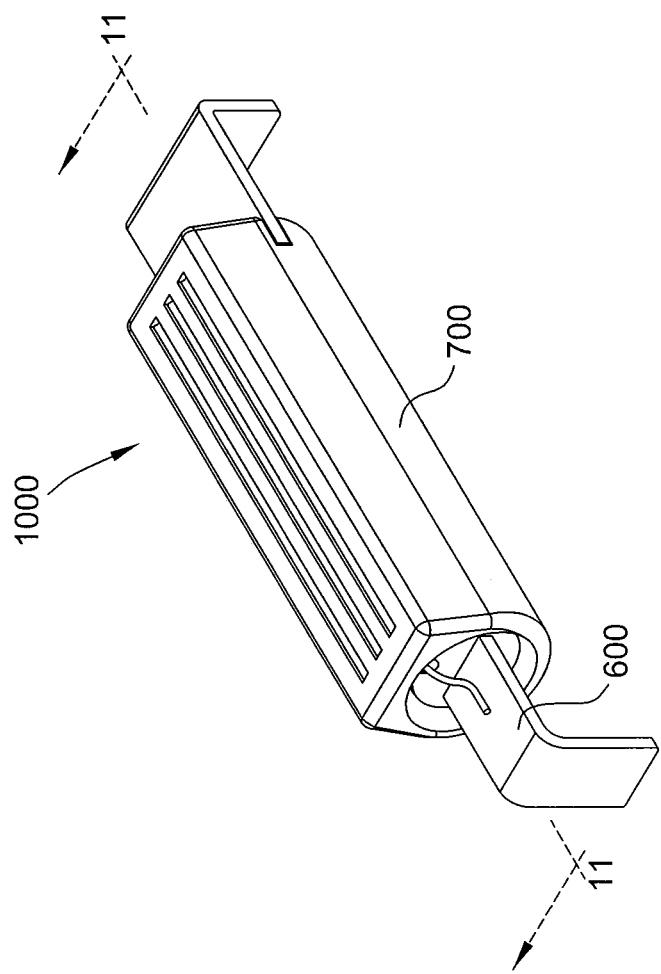
FIG. 10 is a perspective view of an electrode assembly according to one embodiment.
Figure 11:
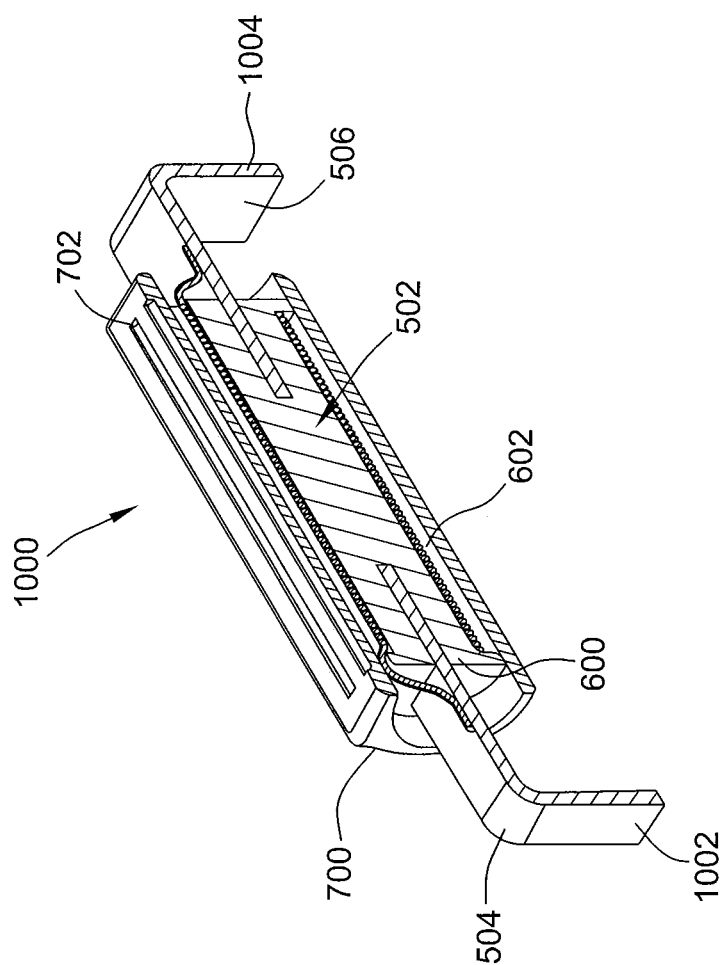
FIG. 11 is a perspective cut-away view of the electrode assembly shown in FIG. 10.

FIG. 10 is a perspective view of an electrode assembly 1000 formed from intermediate assembly 600 and electrode 700. FIG. 11 is a perspective cut-away view of electrode assembly 1000. In electrode assembly 1000, portions of input contact plate 504 and output contact plate 506 are bent at approximately 90° to form first and second tabs 1002 and 1004, respectively. First and second tabs 1002 and 1004 are oriented substantially orthogonal to application surface 702.

Figure 12:
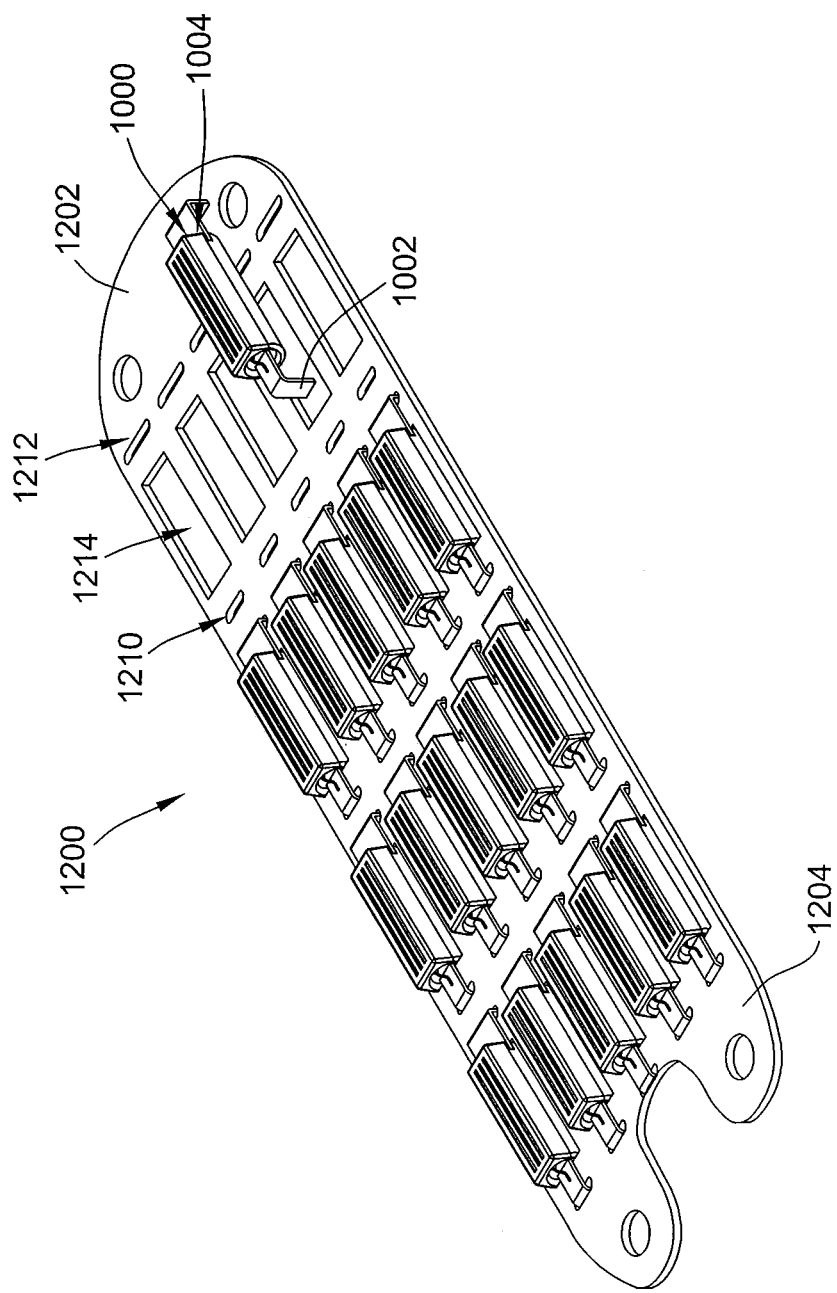
FIG. 12 is a perspective view of a carrier board assembly according to one embodiment.
Figure 13:
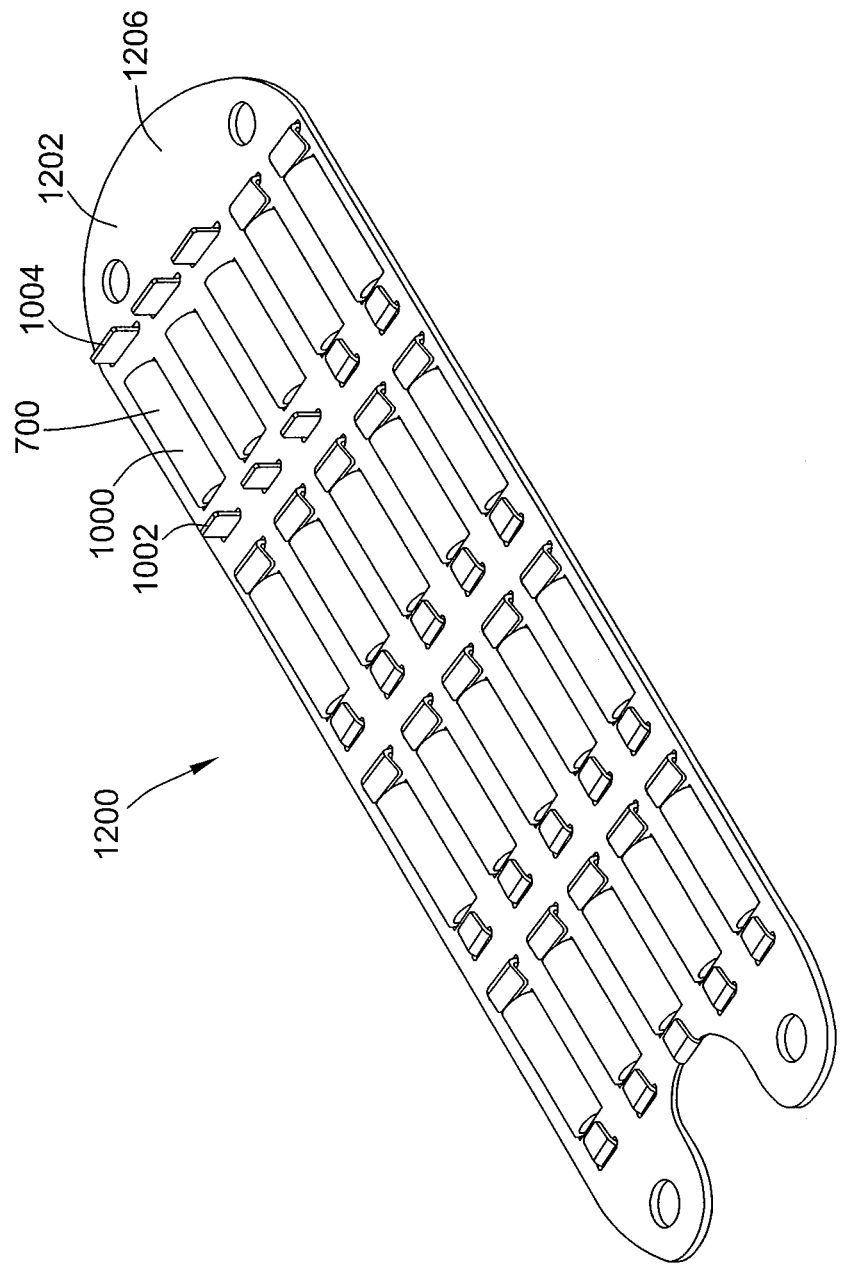
FIG. 13 is a perspective view of the carrier board assembly shown in FIG. 12.

FIGS. 12 and 13 are perspective views of a carrier board assembly 1200. To assemble a paddle lead, a plurality of electrode assemblies 1000 are coupled to a carrier board 1202. Specifically, carrier board 1202 includes a top surface 1204 and an opposite bottom surface 1206. A plurality of first slits 1210, second slits 1212, and slots 1214 are defined through carrier board 1202 and extend from top surface 1204 to bottom surface 1206.

Each first slit 1210 is sized to receive a first tab 1002 of an electrode assembly 1000, each second slit 1212 is sized to receive a second tab 1004 of electrode assembly 1000, and each slot 1214 is sized to receive an electrode 700 of electrode assembly 1000. Accordingly, to couple electrode assembly 1000 to carrier board 1202, first tab 1002 is inserted into first slit 1210 and second tab 1004 is inserted into second slit 1212 such that electrode 700 rests in slot 1214. Once first and second tabs 1002 and 1004 are inserted into the respective first and second slits 1210 and 1212, first and second tabs 1002 and 1004 are bent again at approximately 90°, as shown in FIG. 13. That is, first and second tabs 1002 and 1004 are bent until they are oriented substantially parallel to bottom surface 1206. This process is repeated to couple each electrode assembly 1000 to carrier board 1202.

Figure 14:
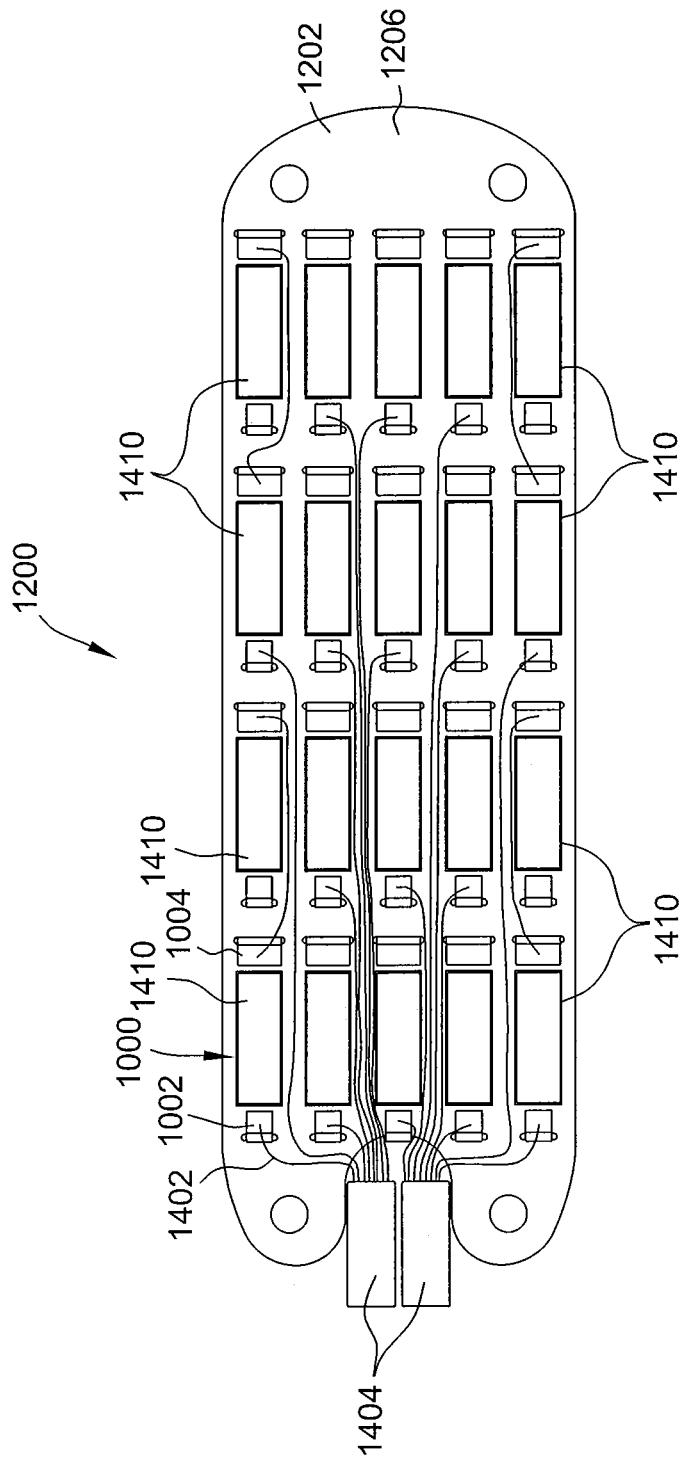
FIG. 14 is a bottom view of a carrier board assembly shown according to one embodiment.

FIG. 14 is a bottom view of carrier board assembly 1200. Channel wires 1402 are electrically coupled to electrode assemblies 1000. Specifically, channel wires 1402 are welded to at least one of first and second tabs 1002 and 1004 of each electrode assembly 1000. Channel wires 1402 extend from a pair of pig tail leads 1404, such as leads 224 (shown in FIGS. 3 and 4). Further, channel wires 1402 connect electrode assemblies 1000 to terminals, such as terminals 218 (shown in FIG. 3). Accordingly, pulse generating circuitry of an IPG, such as IPG 310 (shown in FIG. 4), can be utilized to apply electrical pulses to a patient via electrode assemblies 1000.

As shown in FIG. 14, at least some electrode assemblies 1000 are electrically coupled to one another and to the same terminal 218. In this embodiment, four sets 1410 of electrode assemblies 1000 each include two electrodes assemblies 1000 electrically coupled to one another, and the remaining electrode assemblies 1000 are each independent (i.e., each coupled to their own respective terminal 218). Alternatively, electrode assemblies 1000 may be wired in any configuration that enables carrier board assembly 1200 to function as described herein.

Figure 15:
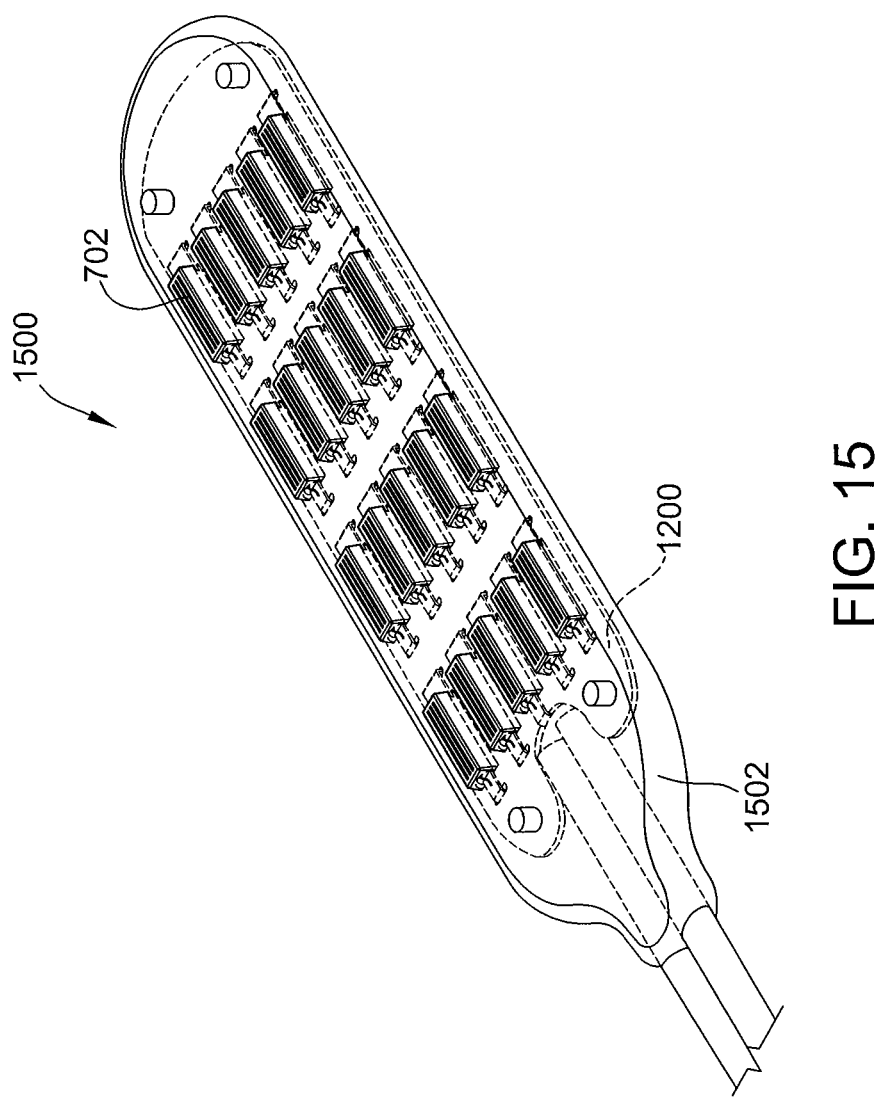
FIG. 15 is a perspective view of a paddle lead according to one embodiment.

FIG. 15 is a perspective view of a paddle lead 1500. To form paddle lead 1500, an over mold 1502 is applied to carrier board assembly 1200 using, for example, either injection molding or compression molding. Over mold 1502 is a non-conductive polymer in this embodiment. As shown in FIG. 15, over mold 1502 substantially encapsulates carrier board assembly 1200, but leaves application surfaces 702 of electrode assemblies 1000 exposed, such that electrical stimulation can be applied to a patient. In some embodiments, the molding process may be performed such that application surfaces 702 are always exposed (i.e., never molded over). Alternatively, molding may initially be applied to application surfaces 702, and after the molding process, mold material is removed and/or trimmed to create windows that expose application surfaces 702.

The design of paddle lead 1500, and more specifically, electrode assemblies 1000, facilitates preventing unwanted heating of electrode assemblies 1000 when paddle lead 1500 is exposed to magnetic fields, for example, from a MRI system. Specifically, winding wire 602 around bobbin 502 forms an inductor 603 that functions as an RF choke. Inductor 603 contains energy (i.e., heat) generated due to magnetic fields. Further, when intermediate assembly 600 is inserted into electrode 700, inductor 603 is substantially surrounded by electrode 700. Accordingly, inductor 603 and electrode 700 are integrated in a single component, and electrode 700 provides shielding and stability for inductor 603. Although a specific embodiment of paddle lead 1500 is shown and described herein, those of skill in the art will appreciate that the systems and methods described herein may be implemented in other types of paddle leads.

Although certain embodiments of this disclosure have been described above with a certain degree of particularity, those skilled in the art could make numerous alterations to the disclosed embodiments without departing from the spirit or scope of this disclosure. All directional references (e.g., upper, lower, upward, downward, left, right, leftward, rightward, top, bottom, above, below, vertical, horizontal, clockwise, and counterclockwise) are only used for identification purposes to aid the reader's understanding of the present disclosure, and do not create limitations, particularly as to the position, orientation, or use of the disclosure. Joinder references (e.g., attached, coupled, connected, and the like) are to be construed broadly and may include intermediate members between a connection of elements and relative movement between elements. As such, joinder references do not necessarily infer that two elements are directly connected and in fixed relation to each other. It is intended that all matter contained in the above description or shown in the accompanying drawings shall be interpreted as illustrative only and not limiting. Changes in detail or structure may be made without departing from the spirit of the disclosure as defined in the appended claims.

When introducing elements of the present disclosure or the preferred embodiment(s) thereof, the articles "a", "an", "the", and "said" are intended to mean that there are one or more of the elements. The terms "comprising", "including", and "having" are intended to be inclusive and mean that there may be additional elements other than the listed elements.

As various changes could be made in the above constructions without departing from the scope of the disclosure, it is intended that all matter contained in the above description or shown in the accompanying drawings shall be interpreted as illustrative and not in a limiting sense.

What is claimed is:

1. An electrode assembly for use in a paddle lead, the electrode assembly comprising:
a bobbin;
an input contact plate coupled to a first end of the bobbin;
an output contact plate coupled to a second end of the bobbin;
a wire wound around the bobbin to form an inductor, wherein a first termination of the wire is electrically coupled to the input contact plate, and wherein a second termination of the wire is electrically coupled to the output contact plate; and
an electrode comprising an application surface and having an aperture defined therethrough, wherein the bobbin is disposed in the aperture such that the inductor is substantially surrounded by the electrode.

2. The electrode assembly of claim 1, wherein the bobbin comprises:
a first disc proximate the first end of the bobbin;
a second disc proximate the second end of the bobbin; and
a body extending between the first and second discs.

3. The electrode assembly of claim 2, wherein at least one of the first disc and the second disc includes a notch defined therein, the notch sized to receive the wire.

4. The electrode assembly of claim 1, wherein the input contact plate has a first width and the output contact plate has a second width that is greater than the first width.

5. The electrode assembly of claim 4, wherein at least one notch is formed in the electrode, the at least one notch configured to engage the output contact plate such that the output contact plate is electrically coupled to the electrode.

6. A paddle lead for applying neurostimulation to a patient, the paddle lead comprising:
- a carrier board;
- a plurality of electrode assemblies coupled to the carrier board; and
- an over mold substantially encapsulating the carrier board and the plurality of electrode assemblies, wherein each of the plurality of electrode assemblies comprises:
  - a bobbin;
  - an input contact plate coupled to a first end of the bobbin;
  - an output contact plate coupled to a second end of the bobbin;
  - a wire wound around the bobbin to form an inductor, wherein a first termination of the wire is electrically coupled to the input contact plate, and wherein a second termination of the wire is electrically coupled to the output contact plate; and
  - an electrode comprising an application surface and having an aperture defined therethrough, wherein the bobbin is disposed in the aperture such that the inductor is substantially surrounded by the electrode.

7. The paddle lead of claim 6, wherein the bobbin comprises:
- a first disc proximate the first end of the bobbin;
- a second disc proximate the second end of the bobbin; and
- a body extending between the first and second discs.

8. The paddle lead of claim 7, wherein at least one of the first disc and the second disc includes a notch defined therein, the notch sized to receive the wire.

9. The paddle lead of claim 6, wherein the input contact plate has a first width and the output contact plate has a second width that is greater than the first width.

10. The paddle lead of claim 9, wherein at least one notch is formed in the electrode, the at least one notch configured to engage the output contact plate such that the output contact plate is electrically coupled to the electrode.

11. The paddle lead of claim 6, wherein the paddle lead includes at least one first slit, at least one second slit, and at least one slot defined therethrough, the at least one first slit sized to receive a first tab formed by the input contact plate, the at least one second slit sized to receive a second tab formed by the output contact plate, and the at least one slot sized to receive the electrode.

12. The paddle lead of claim 6, further comprising a plurality of channel wires electrically coupling the plurality of electrode assemblies to a plurality of terminals.

13. A method for assembling a paddle lead for applying neurostimulation to a patient, the method comprising;
- winding a wire around a bobbin to form an inductor;
- welding a first termination of the wire to an input contact plate that is coupled to a first end of the bobbin;
- welding a second termination of the wire to an output contact plate that is coupled to a second end of the bobbin;
- inserting the bobbin into an aperture defined through an electrode to form an electrode assembly, the bobbin inserted such that the inductor is substantially surrounded by the electrode; and
- coupling the electrode assembly to a carrier board.

14. The method of claim 13, further comprising applying epoxy between the inductor and the electrode to facilitate protecting and securing the inductor.

15. The method of claim 13, wherein inserting the bobbin comprises inserting the bobbin such that one of the input contact plate and the output contact plate engages and electrically couples to the electrode.

16. The method of claim 13, wherein winding a wire comprises passing the wire through a notch formed in the bobbin.

17. The method of claim 13, wherein coupling the electrode assembly to a carrier board comprises:
- bending the input contact plate to form a first tab;
- bending the output contact plate to form a second tab;
- inserting the first tab through a first slit defined in the carrier board;
- inserting the second tab through a second slit defined in the carrier board; and
- bending the first and second tabs to secure the electrode assembly to the carrier board.

18. The method of claim 13, further comprising applying an over mold to the electrode assembly and the carrier board such that the electrode assembly and the carrier board are substantially encapsulated in the over mold.

19. The method of claim 13, further comprising electrically coupling the electrode assembly to a terminal via a channel wire.

20. The method of claim 19, wherein electrically coupling the electrode assembly comprises welding the channel wire to one of the input contact plate and the output contact plate.

* * * * *